(12) United States Patent
Piombini

(10) Patent No.: US 8,400,631 B2
(45) Date of Patent: Mar. 19, 2013

(54) METHOD FOR MEASURING AND METHOD FOR VIEWING A WAVE SURFACE USING SPECTROPHOTOMETRY

(75) Inventor: Hervé Piombini, Esvres sur Indre (FR)

(73) Assignee: Commissariat à l'énergie atomique et aux energies alternatives, Paris (FR)

( * ) Notice: Subject to any disclaimer, the term of this patent is extended or adjusted under 35 U.S.C. 154(b) by 0 days.

(21) Appl. No.: 13/146,392

(22) PCT Filed: Jan. 28, 2010

(86) PCT No.: PCT/EP2010/051009
§ 371 (c)(1),
(2), (4) Date: Oct. 3, 2011

(87) PCT Pub. No.: WO2010/086377
PCT Pub. Date: Aug. 5, 2010

(65) Prior Publication Data
US 2012/0019822 A1  Jan. 26, 2012

(30) Foreign Application Priority Data
Jan. 30, 2009 (FR) .................................. 09 50613

(51) Int. Cl.
*G01J 3/42* (2006.01)
(52) U.S. Cl. ...................................... 356/320
(58) Field of Classification Search .............. 356/300, 356/319–325, 497
See application file for complete search history.

(56) References Cited

U.S. PATENT DOCUMENTS 4,458,323 A * 7/1984 Willis et al. .................... 356/319
4,779,216 A * 10/1988 Collins ............................ 702/94
7,289,225 B2 * 10/2007 De Groot ....................... 356/497

OTHER PUBLICATIONS

H.Piombini and P. Voarino, "Apparatus designed for very accurate measurement of optical reflections" Appl. Opt, 46, 8609-8618 (2007).*
Hervé Piombini a, Stephane Bruynoogheb, Philippe Voarinoc, "Spectral measurement in reflection on steeply aspheric surfaces" Proc. of SPIE vol. 7102.*
International Search Report for PCT/EP2010/051009 mailed Aug. 5, 2010.
French Search Report in French Application No. 09 50613, dated Aug. 21, 2009.
Voarino P et al, "High-accuracy Measurements of the Normal Specular Reflectance" Applied Optics, OSA Optical Society of America, May 1, 2008, Washington, DC., pp. C303-C309, vol. 47 No. 13.
Djurisic A et al, "Progress in the room-temperature optical functions of semiconductors" Materials Science and Engineering Reports, Elsevier Sequoia S.A., Aug. 15, 2002, Lausanne, Switzerland, pp. 237-293, vol. 38, No. 6.

* cited by examiner

*Primary Examiner* — Tarifur Chowdhury
*Assistant Examiner* — Sunghee Y Gray
(74) *Attorney, Agent, or Firm* — Nixon Peabody LLP

(57) ABSTRACT

A method for measuring a wave surface of an optical component formed of a stack of at least two layers of different refraction indices from reflection or transmission measurements of points located on a face of the said optical component.

9 Claims, 3 Drawing Sheets

METHOD FOR MEASURING AND METHOD FOR VIEWING A WAVE SURFACE USING SPECTROPHOTOMETRY

CROSS REFERENCE TO RELATED APPLICATIONS OR PRIORITY CLAIM

This application is a National Phase of PCT/EP2010/051009, filed Jan. 28, 2010, entitled, "METHOD FOR MEASURING AND METHOD FOR VIEWING A WAVE SURFACE USING SPECTROPHOTOMETRY", and which claims priority of, French Patent Application No. 09 50613, filed Jan. 30, 2009, the contents of which are incorporated herein by reference in their entirety.

TECHNICAL FIELD

The present invention concerns a method for measuring the wave surface of an optical component, and also a method for viewing the wave surface of an optical component.

The measuring method according to the invention allows, in particular, measurement of the deformations of the wave surface of a treated optical component, relating to the heterogeneities of the surface treatments applied to this optical component when it is functionalised, while the method of viewing the wave surface allows, in particular, the said deformations to be located.

STATE OF THE PRIOR ART

Inspection of the wave surface of an optical component, whether or not treated, is traditionally accomplished using an interferometer, which is often of the Fizeau type. With this interferometer a reference wave surface is compared with the wave surface to be measured.

If the optical component is untreated the wave surface measured by the interferometer is equal, plus or minus a factor:
- either to the deformation of the surface of the optical component, when a reflection measurement is made;
- or to the measurement of the optical path difference, relating to the optical component traversed (heterogeneity of thickness and/or of refraction index), in the case of a transmission measurement.

If the optical component is treated, i.e. if it includes a surface treatment such as an anti-glare or a filter such as, for example, a mirror, a separator, a dichroic or a polariser, it is then also necessary to take into account the response of the treatment, which corresponds to a phase plate.

However, there are few interferometers which enable the wave surface of a treated optical component to be measured if this treatment is not centred on 633 nm or 1064 nm. As a result, the type of treated optical components the wave surface of which (and in particular the deformation of the wave surface of which) it is possible to measure by interferometry is very limited.

In addition, interferometry is limited in terms of accuracy to the reference planes used, specifically an accuracy of between $\lambda/10$ and $\lambda/50$.

In addition, interferometry takes account of the quality of the initial substrate, and also of the stresses caused by the treatments and undergone by the optical component.

The inventor has therefore set himself the aim of devising a method enabling the wave surface of a treated optical component to be measured, and a method enabling it to be viewed, and in particular allowing viewing of the deformation of the wave surface relating to the treatment deposited on the optical component, mostly of which treatments being optical treatments able to be deposited on an optical component.

PRESENTATION OF THE INVENTION

This aim is achieved by a method for measuring a wave surface derived from a zone of a face of an optical component formed of a stack including a substrate and at least one layer having different refraction indices, wherein the method includes the following steps:
a) measuring, at a reference point $M_O$ located in the zone of the face of the optical component, the spectral response of the said reference point as a function of the wavelength of a light passing through the said reference point, and grouping together the measurements obtained in this manner in a spectrum representing the spectral response as a function of the wavelength;
b) in the spectrum obtained in step a), determining which portion of this spectrum is the one for which the difference between a successive minimum and maximum, or between a successive maximum and minimum, of the spectrum is greatest, and selecting a wavelength, called the measurement wavelength $\lambda_{meas}$, from among the wavelengths corresponding to this portion of the spectrum;
c) measuring the spectral response (called below "RSP") of n measuring points $M_i$ located in the said zone, where n is an integer greater than or equal to 1, at the measurement wavelength $\lambda_{meas}$: $RSP_{(Mi)}(\lambda_{meas})$:
d) among the measurements obtained in step c), determining the average spectral response to the measurement wavelength: $RSP_{av}(\lambda_{meas})$;
e) in the spectrum of reference point $M_O$ obtained in step a), determining the average wavelength $\lambda_{av}$ such that $RSP_{Ref(Mo)}(\lambda_{av})=RSP_{av}(\lambda_{meas})$;
f) for each of the n points $M_i$, with i=1 to n:
  1) determining the wavelength X, such that the spectral response at point $M_i$ to the measurement wavelength is equal to the spectral response at reference point $M_O$ to the wavelength $\lambda_i$:

$$RSP_{Mi}(\lambda_{meas})=RSP_{Ref(Mo)}(\lambda_i)$$

2) calculating the difference between the wave number $\sigma_i$ ($\sigma_i=1/\lambda_i$) and the average wave number $\sigma_{av}$ ($\sigma_{av}=1/\lambda_{av}$):

$$\Delta\sigma_i=\sigma_i-\sigma_{av}$$

3) determining the real centring wave number $\sigma_j$ at point $M_i$:

$$\sigma_j=\sigma_{centering}+\Delta\sigma_i$$

with $\sigma_{centring}=1/\lambda_{centring}$ and $\lambda_{centring}$ being the centring wavelength of the optical component;
  4) calculating the wavelength $\lambda_j$ corresponding to the real centring wave number at point $M_i$:

$$\lambda_j=1/\sigma_j$$

5) calculating the phase difference $\Delta\Phi_{Mi}$ existing between the real centring phase $\Phi(\lambda_j)$ and the theoretical centring phase $\Phi(\lambda_{centring})$ at the centring wavelength:

$$\Delta\Phi_{Mi}=\Phi(\lambda_j)-\Phi(\lambda_{centring})$$

6) calculating the path difference $\delta_i$ existing at point $M_i$ at the centring wavelength:

$$\delta_i=\Delta\Phi_{Mi}\times\lambda_{centring}/(2\pi).$$

The skilled man in the art knows how to determine the centring wavelength of an optical component including a substrate and at least one layer. The transmission or reflection spectrum of the optical component is in fact produced as a function of the wave number and the centring wave number is the wave number at the level of which the spectrum represented in wave numbers is approximately symmetrical. The centring wavelength is then equal to the inverse of the centring wave number ($1/\sigma_{centring}$).

The spectrum obtained in step a) is preferably produced over a range of wavelengths such that the difference between the lowest wavelength and the highest wavelength in this range of wavelengths is at least equal to 0.2 times the centring wavelength of the optical component.

The stack advantageously includes m layers, where m is an integer greater than or equal to 2, and where the adjacent layers among the m layers have different refraction indices. It should be noted that each stack layer can have a different thickness.

The calculation of the phase difference $\Delta\Phi_{Mi}$ existing between the real centring phase $\Phi(\lambda_j)$ and the theoretical centring phase $\Phi(\lambda_{centring})$ in step 6) of the method can be obtained by every method for calculating stacking of thin layers.

According to a first variant, the calculation of the phase difference $\Delta\Phi_{Mi}$ existing between the real centring phase $\Phi(\lambda_j)$ and the theoretical centring phase $\Phi(\lambda_{centring})$ in step 6) of the method is accomplished using a matrix method, such as for example the Abeles formalism.

According to a second variant, the calculation of the phase difference $\Delta\Phi_{Mi}$ existing between the real centring phase $\Phi(\lambda_j)$ and the theoretical centring phase $\Phi(\lambda_{centring})$ in step 6) of the method is accomplished using a vector method, such as for example the Schmith method.

The Abeles formalism and the Schmith method are, respectively, a matrix method and a vector method well known to the skilled man in the art, which enable, on the basis of the thickness parameters and refraction indices of the different layers of a stack of layers, the transmission, phase variations and absorption of this stack to be determined.

The measurement wavelength $\lambda_{meas}$ is advantageously the wavelength for which the portion of the said spectrum obtained in step a) has an inflection point.

According to a first variant, the RPS spectral response is a reflection.

According to a second variant, the RPS spectral response is a transmission.

The n measurement points $M_i$ are advantageously distributed uniformly in the zone to be measured. The n measurement points $M_i$ are preferably equidistant.

The invention also concerns a method of viewing a wave surface of a zone of a face of an optical component including a substrate and at least one layer having different refraction indices. The viewing method includes the steps of the measurement method described above, and also includes a step g), located after the steps of the measurement method, consisting in placing the n path differences $\delta_i$ of the n $M_i$ points according to the spatial coordinates ($x_i$, $y_i$) of the said n points in the zone. By this means a mapping of the path differences is obtained, corresponding, plus more minus a $2\pi/\lambda$ factor, to a mapping of the wave surface. This viewing method therefore includes the measurement of the path difference at each of the points $M_i$ located in the zone of the face of the optical component to be studied and the placing of these measurements at the locations of the zone where they have been made.

BRIEF DESCRIPTION OF THE DRAWINGS

The invention will be better understood and other advantages and features will appear on reading the following description, which is given as a non-restrictive example, accompanied by the appended figures, among which.

DETAILED DESCRIPTION OF PARTICULAR EMBODIMENTS

The principle of the measurement method according to the invention is based on the observation that all spatial heterogeneities of an optical component consisting of a stack of layers can be represented by a variation of the local centring wavelength of the stack, which produces a phase variation.

We shall illustrate the principle of the invention by producing the wave surface mapping of an optical component which is a dielectric mirror (for example, a Bragg mirror).

The dielectric mirror chosen to illustrate this example consists of a substrate supporting 23 layers of alternating refraction indices $n_H$ and $n_B$, where $n_H$ is the index of the high-index layers and $n_B$ is the index of the low-index layers. This may, for example, be a band-pass filter in the near-infrared domain, consisting of a stack of an alternating thin dielectric layers of high refraction index and of low refraction index layers, deposited on a glass support.

In this case the substrate is, for example, made of borosilicate and has a refraction index of 1.51, the index layers $n_H$ are zirconia layers of refraction index 1.68 and the index layers $n_B$ are silica layers of refraction index 1.22. It is also stipulated that the layers are deposited in this case by a sol-gel process.

The first step is to measure the spectral response (reflection or transmission, as desired) of the optical component to be tested at a point of the component, taken as reference point $M_O$, over quite a broad field of wavelengths. The spectrum thus obtained will enable the centring wavelength and the half-width of the optical component to be determined. It is stipulated that, in order to determine the centring wavelength and the half-width of the optical component, it is equally possible to study either the reflection or the transmission spectrum of the optical component (if the substrate is transparent): the same values will be obtained.

Figure 1:
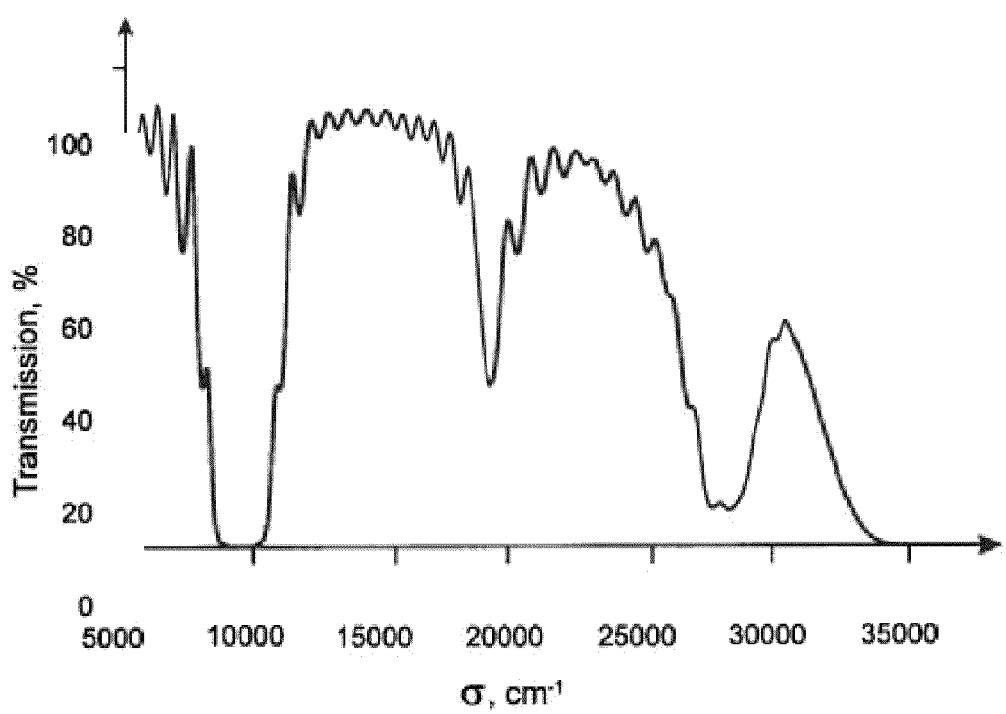
FIG. 1 represents the spectral transmission response of a mirror of formula $S(HB)^{11}H$ as a function of the wave number.

As an example, the spectral transmission response of the optical component to be tested over a range of wave numbers from 5000 to 35000 $cm^{-1}$ (i.e. a wavelength of 286 nm to 2000 nm) is represented in FIG. 1.

On the basis of this transmission spectrum, it can be deduced that the optical component to be tested has a centring wave number $\sigma_{centring}$ equal to 9500 $cm^{-1}$ (i.e. a centring wavelength $\lambda_{centring}$ of 1052 nm). It is also observed that this component has an index ratio $n_H/n_B$ equal to 1.37 and that it indeed has 23 layers.

Figure 2:
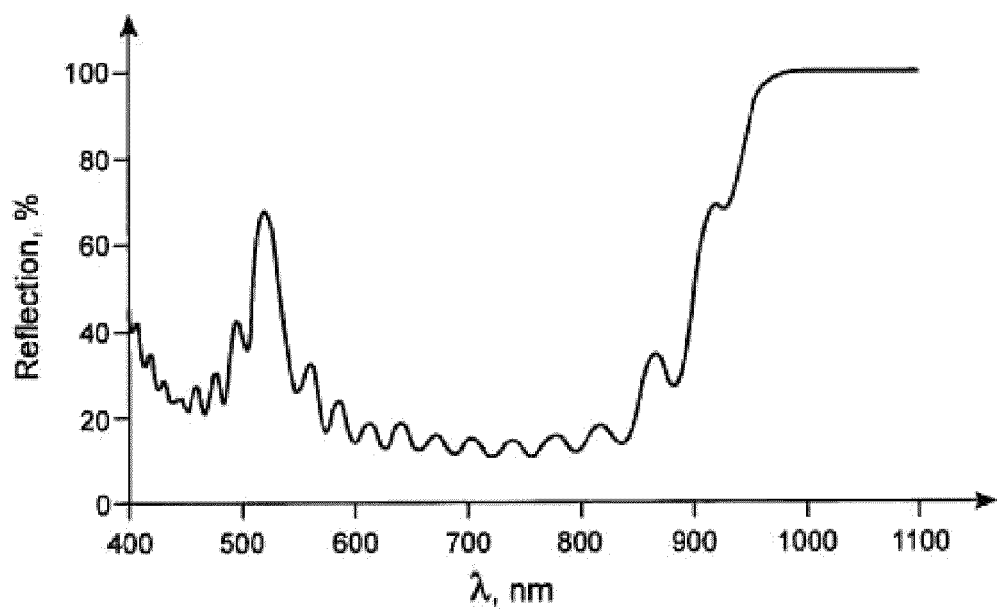
FIG. 2 represents the spectral reflection response of a mirror of formula $S(HB)^{11}H$ as a function of the wavelength.

In our example the choice is made to produce the spectral reflection response of a point of the optical component to be tested over a range of wavelengths from 400 nm to 950 nm:

this spectral reflection response will be considered as being the reference spectral reflection response $R_{ref(Mo)}$ and is represented in FIG. 2.

The optical properties (reflection, transmission, phase variation) of such an optical component can be simulated by a stack of formula $S(HB)^{11}H$, where S represents the substrate, H represents a refraction index layer $n_H$ and B represents a refraction index layer $n_H$, calculated, for example, using the Abeles formulae. The Abeles formalism will be particularly useful for calculating the phase variations of the optical component, as we shall see below.

In the reflection spectrum produced at reference point $M_O$ (FIG. 2), it is determined which of the two differences, whether between a successive minimum (trough of the oscillation) and maximum (peak of the oscillation), or between a successive maximum and minimum of the spectrum, is the greater. In fact, the maximum difference between two successive extrema of the spectrum are determined, where both extrema are a minimum and a maximum. A wavelength is then chosen from among the wavelengths corresponding to the portion of spectrum between the minimum and the maximum or the maximum and minimum of this maximum difference determined in this manner. This wavelength (called the measurement wavelength) will subsequently be used to produce the mapping of the spectral response of a zone of the optical component, where this zone includes the reference point and can, for example, represent the entire face of the optical component.

In order to obtain satisfactory accuracy in terms of the measurements of the optical component's heterogeneities, the measurement wavelength is preferably chosen in the rise and fall fronts of the spectral response of the optical component, usually at the inflection point.

In FIG. 2 it can be seen that, among the spectrum's inflection points, the one located at 900 nm is located on a rise front the gradient of which seems the steepest. In addition, at 900 nm, reflection is average and equal to 40%. In fact, what is important for the choice of measurement wavelength is to have the largest spectral field in which the reflection or transmission coefficient varies in linear fashion with the wavelength, with a non-zero variation. In the spectrum represented in FIG. 2 it is thus observed that 900 nm can therefore be a measurement wavelength $\lambda_{meas}$ which is suitable to represent the wave surface of the optical component.

Figure 3:
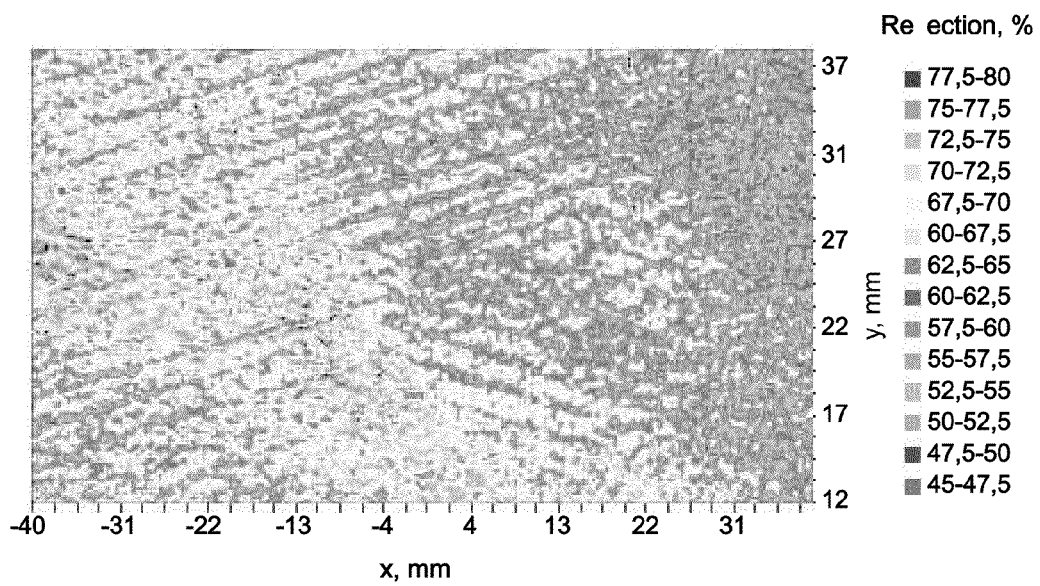
FIG. 3 represents the reflection mapping of the mirror of formula $S(HB)^{11}H$ over a zone of 79×26 $mm^2$ at 900 nm.

After having chosen the measurement wavelength, a reflection mapping at the measurement wavelength $\lambda_{meas}$ of the zone of the optical component in which it is desired to measure the wave surface is then produced. In FIG. 3 a reflection mapping produced at a wavelength of 900 nm over a zone of 79×26 mm$^2$ of the dielectric mirror to be tested of formula $S(HB)^{11}H$ is represented.

Before transforming the reflection measurements of this reflection mapping into wave surface measurements, it may be necessary to process the reflection measurements using linear or non-linear filters, for example a filter of the averaging type or a filter of the median type, in order to eliminate real residual local faults (scratches, holes, etc.), or faults due to the presence of dust on the surface of the optical component.

The principle of an averaging filter consists in replacing a measurement made at point A by a weighted average of the measurements made in the points adjacent to point A.

The principle of a median filter consists in replacing a measurement made at point A by the median value of all the measurements made at the points located in a window centred on point A.

Figure 4:
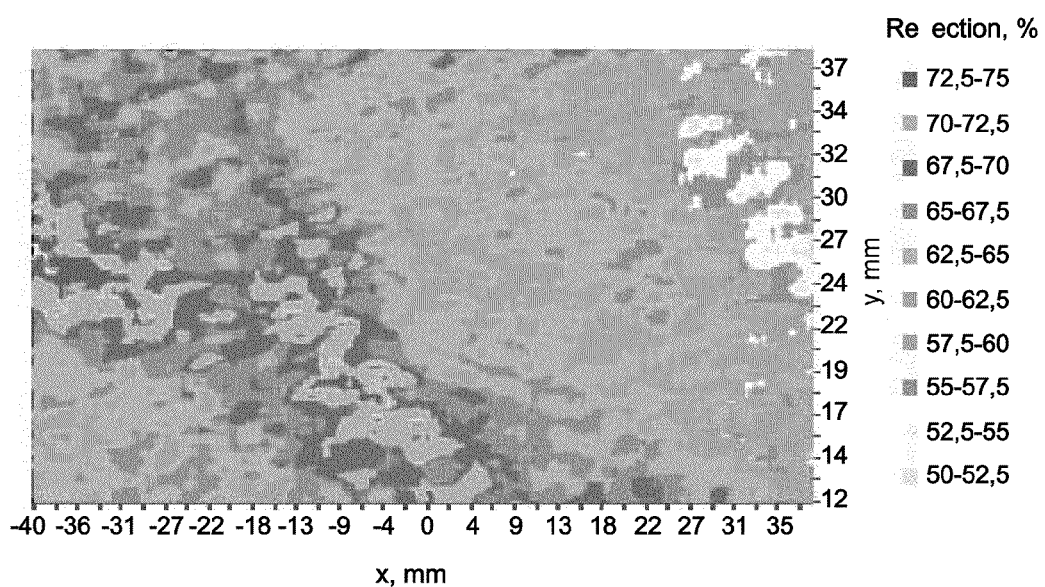
FIG. 4 represents a spectral reflection response mapping after an order 5 median filtering.

For example, FIG. 4 represents the reflection mapping of FIG. 3 after an order 5 median filtering.

Transformation of the reflection mapping into a wave surface mapping is obtained by determining, for each point $M_i$ of the optical component, its difference compared to the theoretical centring. This difference relative to the theoretical centring is then transformed into phase shift $\Phi$. This phase shift $\Phi$ is in its turn transformed into a path difference $\delta$. The path difference $\delta$ may be transformed into a mechanical thickness, by multiplying the path difference $\delta$ by a factor equal to 0.5 (if this is a spectral reflection response) or to 1 (if this is a spectral transmission response). The mapping of the wave surface of the optical component may be viewed by producing a path or "mechanical thickness" mapping.

The phase shift $\Phi$ may be obtained by using the Abeles matrix formalism. Indeed, the Abeles formalism enables the reflection, transmission and absorption to be obtained, together with the phase of a stack of optical layers. This formalism consists of simple multiplications of 2×2 matrices, using one matrix for each optical layer considered.

Figure 5:
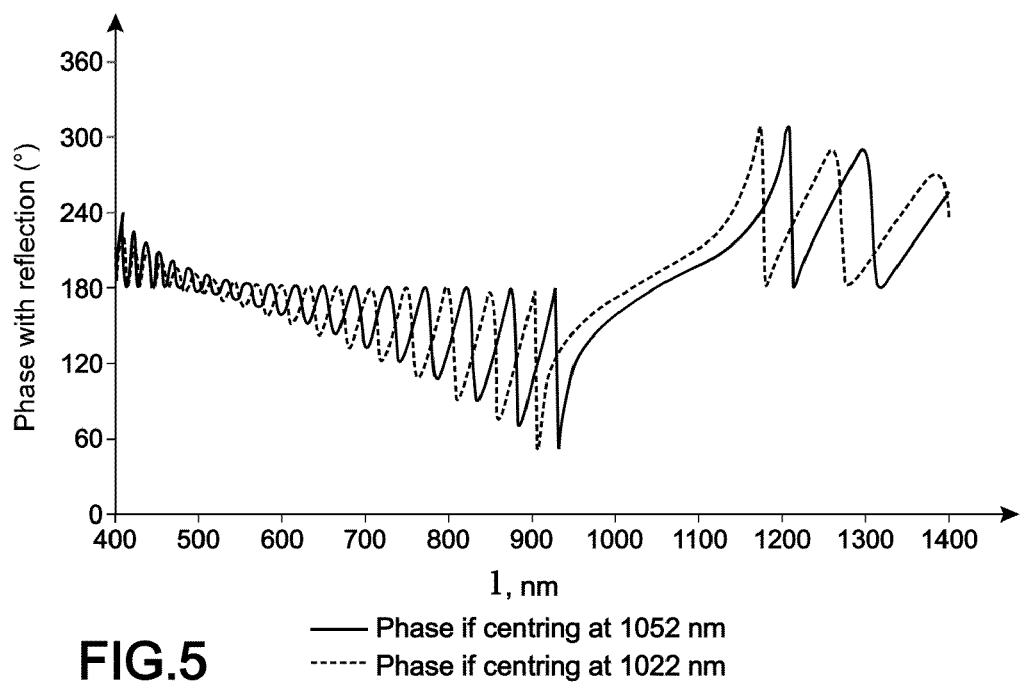
FIG. 5 represents the phase variation as a function of the wavelength of a mirror $S(HB)^{11}H$ having an index ratio of 1.37 for a centring at 1052 nm and for a centring at 1022 nm.

As an illustration, FIG. 5 shows the spectral changes of the theoretical reflection phase of a dielectric mirror of formula $S(HB)^{11}H$ having an index ratio of 1.37, when the mirror has a centring wavelength at 1052 nm and when it has a centring wavelength at 1022 nm (dotted line). Using this data it is possible to deduce the phase difference $\Delta\Phi$ existing when the mirror is heterogeneous and when, instead of having a centring wavelength at 1052 nm, it in fact has a real centring wavelength of 1022 nm. A mirror having such a spatial heterogeneity will have a phase variation at the operating wavelength, for example 1054 nm, $\Delta\Phi(1054)=\Phi_{1052}(1054)-\Phi_{1022}(1054)=11°35$, where this value may be expressed as a path difference (or difference of optical path) by the relationship $\Delta\Phi=360\times\delta/\lambda$, in this case 33 nm, and where this value is equivalent to a "mechanical thickness" of 16.5 nm.

The procedure to measure and view a wave surface according to the invention is summarised below.

Firstly, a reflection [transmission] spectrum is produced as a function of the wavelength at a point $M_O$, located in the zone of the optical component concerning which it is desired to know the effect of a treatment on its wave surface; this point $M_O$ is chosen as the reference point. In this spectrum a measurement wavelength $\lambda_{meas}$ is then selected and the reflection is measured at n measurement points $M_i$ located in the zone to be studied of the optical component at the measurement wavelength $\lambda_{meas}$ (where n is an integer greater than or equal to 1 and i=1 to n): $R_{(Mi)}(\lambda_{meas})$. For example, in the case of a zone having an area of 79×26 mm$^2$, in this case 179 points are made for 105 measuring points.

The average of all these measurement points is calculated, and by this means the average reflection [transmission] is determined at the measurement wavelength in the measurement zone: $R_{av}(\lambda_{meas})$ [$T_{av}(\lambda_{meas})$].

It is then sought, in the reflection reference [transmission] spectrum at point $M_O$, to find the wavelength (called the average wavelength $\lambda_{av}$) at which the average reflection [transmission] at the measurement wavelength is equal to the reference reflection [transmission] at point $M_o$ at the average wavelength, i.e. $R_{av}(\lambda_{meas})=R_{Ref(Mo)}(\lambda_{av})$ [$T_{av}(\lambda_{meas})=T_{Ref(Mo)}(\lambda_{av})$].

This then enables the average wave number to be obtained: $\sigma_{av}=1/\lambda_{av}$.

Following this, for each of the n points $M_i$, the following steps are accomplished:
using the reference spectrum at point $M_O$ the wavelength $\lambda_i$ is determined for which the reflection [transmission] at point $M_i$ at the measurement wavelength is equal to the reference reflection [transmission] at point $M_O$ at the wavelength $\lambda_i$:

$$R_{Mi}(\lambda_{meas}) = R_{Ref(Mo)}(\lambda_i)$$

$$[T_{Mi}(\lambda_{meas}) = T_{Ref(Mo)}(\lambda_i)]$$

the wave numbers $\sigma_i$ corresponding to the wavelengths $\lambda_i$ are calculated:

$$\sigma_i = 1/\lambda_i$$

the differences between the wave numbers $\sigma_i$ and the average wave number $\sigma_{av}$ are calculated:

$$\Delta\sigma_i = \sigma_i - \sigma_{av}$$

the real centring wave number $\sigma_j$ at point $M_i$ relative to the centring wave number $\sigma_{centring}$ is determined:

$$\sigma_j = \sigma_{centring} + \Delta\sigma_i$$

the real centring wavelength $\lambda_j$ corresponding to the real centring wave number at point $M_i$ is calculated:

$$\lambda_j = 1/\sigma_j$$

the theoretical phase difference $\Delta\Phi_{Mi}$ existing between the real centring phase $\Phi(\lambda_j)$ and the theoretical centring phase $\Phi(\lambda_{centring})$ is calculated:

$$\Delta\Phi_{Mi} = \Phi(\lambda_j) - \Phi(\lambda_{centring})$$

the path difference $\delta_i$ existing at point $M_i$ is calculated:

$$\delta_i = \Delta\Phi_{Mi} \times \lambda_{centring}/(2\pi)$$

The path differences $\delta_i$ obtained for each of the points $M_i$ can then be multiplied by a factor F, according to whether the wave is reflected (F=0.5) or transmitted (F=1), which enables the "equivalent mechanical thickness" at each point $M_i$ to be obtained.

Figure 6:
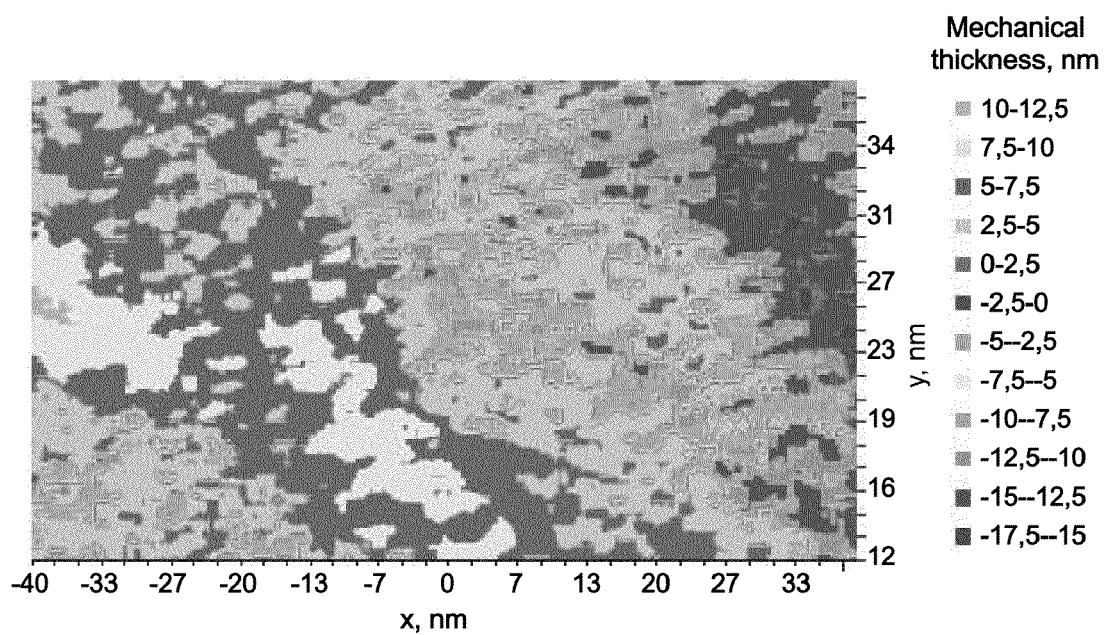
FIG. 6 represents the wave surface mapping derived from the reflection mapping illustrated in FIG. 4, expressed as "mechanical thickness" in nm.

When these path differences $\delta_i$ or these "equivalent mechanical thicknesses" are available, in the geographical coordinates of the points $M_i$ to which they are related, it is then possible to produce a mapping representing the wave surface. It is thus possible to view the wave surface. Such a wave surface mapping expressed as mechanical thickness is represented in FIG. 6. In this FIG. 6 the mechanical thicknesses are expressed in nanometers (see the grey scale at the right).

It should be noted that the above examples concern spectral reflection responses. However, it is perfectly possible to produce, using the same principle, a wave surface mapping of an optical component using a spectral transmission response (see the above passages in square brackets).

In addition, the methods according to the invention can be applied to optical components other than the one described above, for example stacks of general formula $S(H_k B_l)^m$, in which the $H_k$ terms are layers with high refraction indices having a thickness $e_k$, the $B_l$ terms are layers with low refraction indices having a thickness $e_l$, S is the substrate and m is the number of layers of the stack. The optical component to be tested need merely be a stack of alternate optical layers of two different refraction indices, and a matrix formalism, such as for example the Abeles formalism, can then be used to calculate the phase variations of the optical component.

The originality of the method according to the invention is that it provides data in terms of wave surface by means of spectrophotometric measurements, i.e. by means of reflection or transmission measurements.

The method of measuring the wave surface of an optical component according to the invention enables the deformation of the wave surface of an optical component, relating to the heterogeneity of the treatment deposited on the component, to be measured, and thus the modifications of the wave surface of an optical component to be viewed, whatever its operating wavelength. This enables, in particular, the presence of heterogeneities caused by the physical or chemical deposit of one or more thin layers on the component to be located. The method according to the invention thus enables the deformation of the wave surface relating solely to the optical treatments of the optical component to be checked by studying the wave surface derived from this component after a reflection or a transmission, regardless of the nature of the component's polishing and of the stresses of the optical treatment applied to the component.

Such a measurement method is particularly useful to check optical components undergoing dielectric treatments and including many layers, such as for example filters (polarisers or mirrors), the satisfactory operation of which requires the presence of a uniform wave surface.

The invention claimed is:

1. A method for measuring a wave surface derived from a zone of a face of an optical component formed of a stack including a substrate and at least one layer having different refraction indices, wherein the method includes the following steps:

a) measuring, at a reference point $M_O$ located in the zone of the face of the optical component, a spectral response of the said reference point as a function of a wavelength of a light passing through the said reference point, and grouping together the measurements obtained in this manner in a spectrum representing the spectral response as a function of the wavelength;

b) in the spectrum obtained in step a), determining a range of wavelengths which gives the greatest difference between a successive minimum and maximum, or between a successive maximum and minimum of the spectral response and selecting a wavelength, and selecting a wavelength, wavelength, called a measurement wavelength, from among the determined range of wavelengths;

c) measuring the spectral response of n measuring points $M_i$ located in the said zone, where n is an integer greater than or equal to 1, at the measurement wavelength $\lambda_{meas}$:

$$RSP_{(Mi)}(\lambda_{meas}):$$

d) among the measurements obtained in step c), determining an average spectral response to the measurement wavelength: $RSP_{av}(\lambda_{meas})$;

e) in the spectrum of reference point $M_O$ obtained in step a), determining the average wavelength $\lambda_{av}$ such that $RSP_{Ref(Mo)}(\lambda_{meas})$;

f) for each of the n points $M_i$, with i=1 to n:

1) determining a wavelength $\lambda_i$ such that the spectral response at point $M_i$ to the measurement wavelength is equal to the spectral response at reference point $M_O$ to the wavelength $\lambda_i$:

$$RSP_{Mi}(\lambda_{meas}) = RSP_{Ref(Mo)}(\lambda_i)$$

2) calculating a difference between a wave number σi (σi=1/λi) and the average wave number $\sigma_{av}$ ($\sigma_{av}=1/\lambda_{av}$):

$$\Delta\sigma_i = \sigma_i - \sigma_{av}$$

3) determining a real centering wave number $\sigma_j$ at point Mi:

$$\sigma j = \sigma centering + \Delta\sigma i$$

with $\sigma_{centering} = 1/\lambda_{centering}$ and $\lambda_{centering}$ being a centering wavelength of the optical component;

4) calculating a wavelength $\lambda_j$ corresponding to the real centering wave number at point $M_i$:

$$\lambda_j = 1/\sigma_j$$

5) calculating a phase difference $\Delta\phi_{Mi}$ existing between a real centering phase and a theoretical centering phase at the centering wavelength:

$$\Delta\Phi_{Mi} = \Phi(\lambda_j) - \Phi(\lambda_{centering})$$

6) calculating a path difference $\delta_i$ existing at point $M_i$ at the centering wavelength:

$$\delta_i = \Delta\Phi_{Mi} \times \lambda_{centring}/(2\pi).$$

2. A method for measuring a wave surface according to claim 1, wherein the stack includes m layers, where m is an integer greater than or equal to 2, and where adjacent layers among the m layers have different refraction indices.

3. A method for measuring a wave surface according to claim 1, wherein the calculation of the phase difference $\Delta\Phi_{Mi}$ existing between the real centering phase $\phi(\lambda_j)$ and the theoretical centering phase $\phi(\lambda_{centering})$ in step 6) is accomplished using a matrix method, such as for example the Abeles formalism.

4. A method for measuring a wave surface according to claim 1, wherein the calculation of the phase difference $\Delta\Phi_{Mi}$ existing between the real centering phase $\phi(\lambda_j)$ and the theoretical centering phase $\phi(\lambda_{centering})$ in step 6) is accomplished using a vector method, such as for example the Schmith formalism.

5. A method for measuring a wave surface according to claim 1, wherein the measurement wavelength $\lambda_{meas}$ is the wavelength for which the portion of the said spectrum obtained in step a) has an inflection point.

6. A method for measuring a wave surface according to claim 1, wherein the RPS spectral response is a reflection.

7. A method for measuring a wave surface according to claim 1, wherein the RPS spectral response is a transmission.

8. A method for measuring a wave surface according to claim 1, wherein the n measuring points $M_i$ are distributed uniformly in the zone to be measured.

9. A method for viewing a wave surface of a zone of a face of an optical component including a substrate and a least one layer having different refraction indices, wherein said method includes the steps of the measurement method according to claim 1, and further includes a step g) consisting in placing the n path differences $\delta_i$ of the n points $M_i$ according to the spatial coordinates $(x_i, y_i)$ of the said n points in the zone.

* * * * *

UNITED STATES PATENT AND TRADEMARK OFFICE
CERTIFICATE OF CORRECTION

PATENT NO.       : 8,400,631 B2                                          Page 1 of 1
APPLICATION NO.  : 13/146392
DATED            : March 19, 2013
INVENTOR(S)      : Hervé Piombini It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 45 days.

Signed and Sealed this
First Day of September, 2015

Michelle K. Lee
*Director of the United States Patent and Trademark Office*